United States Patent [19]

Bello et al.

[11] Patent Number: 5,571,079
[45] Date of Patent: Nov. 5, 1996

[54] WOUND DRESSING

[75] Inventors: Gastone P. Bello, Manmouth Beach; John W. Lyle, Belmar; Donald A. Johnson, Sea Girt, all of N.J.

[73] Assignee: Algos Pharmaceutical Corporation, Neptune, N.J.

[21] Appl. No.: 366,670

[22] Filed: Dec. 30, 1994

[51] Int. Cl.$^6$ ......................................................... A61F 5/00
[52] U.S. Cl. .............................. 602/46; 602/48; 602/52; 602/54; 602/56; 604/304; 604/307
[58] Field of Search ......................... 602/41–59; 604/304, 604/305, 306, 307, 308

[56] References Cited

U.S. PATENT DOCUMENTS

| | | |
|---|---|---|
| 2,858,830 | 11/1958 | Rogins . |
| 3,025,854 | 3/1962 | Scholl . |
| 3,062,210 | 11/1962 | Scholl . |
| 3,113,568 | 12/1963 | Robins . |
| 3,156,242 | 11/1964 | Crowe, Jr. . |
| 3,157,178 | 11/1964 | Bentov . |
| 3,665,918 | 5/1972 | Lindquist et al. . |
| 3,900,027 | 8/1975 | Keedwell . |
| 3,949,742 | 4/1976 | Nowakowski . |
| 3,975,567 | 8/1976 | Lock . |
| 3,978,855 | 9/1976 | McRae et al. . |
| 4,450,833 | 5/1984 | Brooks et al. . |
| 4,530,353 | 7/1985 | Lauritzen . |
| 4,655,210 | 4/1987 | Edenbaum et al. . |
| 4,733,659 | 3/1988 | Edenbaum et al. . |
| 4,773,409 | 9/1988 | Cilento et al. . |
| 4,810,582 | 3/1989 | Gould et al. . |
| 4,906,240 | 3/1990 | Reed et al. . |
| 4,960,594 | 10/1990 | Honeycutt . |
| 5,098,500 | 3/1992 | Reed et al. . |
| 5,354,261 | 10/1994 | Clark et al. ............................... 602/58 |
| 5,393,528 | 2/1995 | Staab . |

*Primary Examiner*—Richard J. Apley
*Assistant Examiner*—Kim M. Lee
*Attorney, Agent, or Firm*—Dilworth & Barrese

[57] ABSTRACT

A wound dressing possessing a wound exudate-absorbing component and at least one liquid-impermeable dressing-securing component is manufactured from the same flexible, cellular, thermoplastic resin workpiece.

10 Claims, 1 Drawing Sheet

U.S. Patent  Nov. 5, 1996  5,571,079
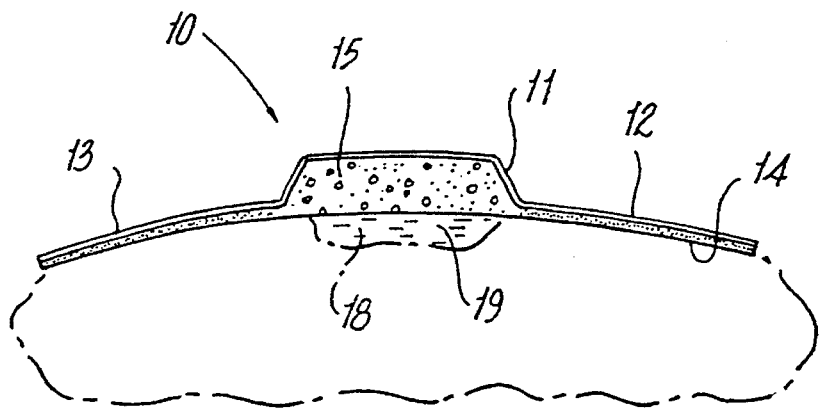
Fig. 1
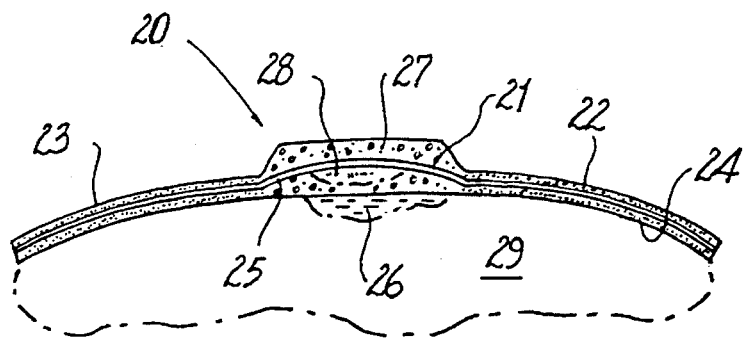
Fig. 2
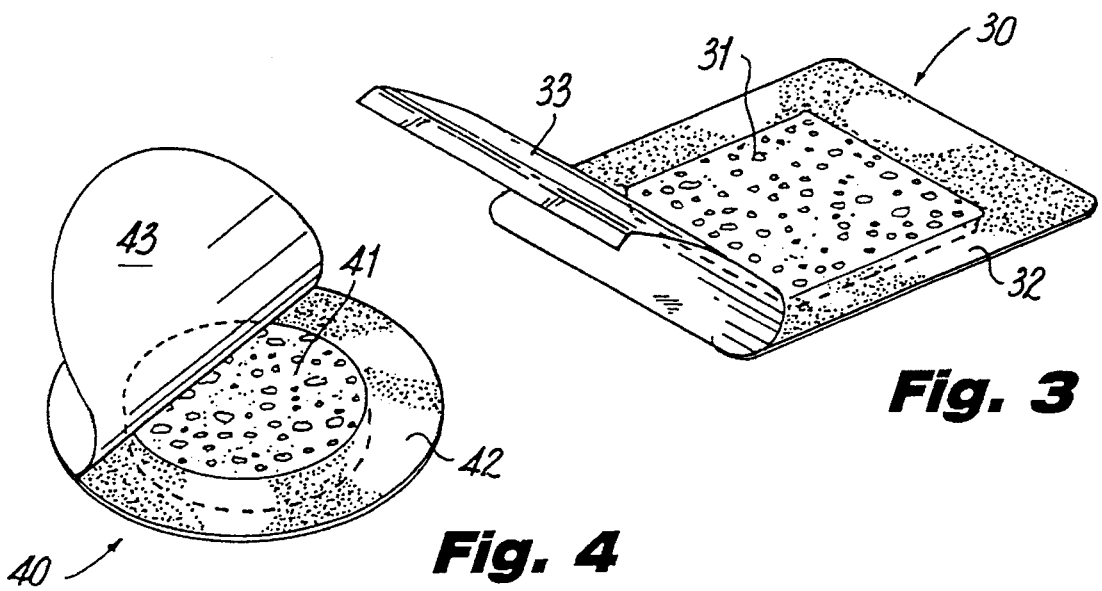
Fig. 3
Fig. 4 ns and greater moisture vapor permeability in its adhesive tab portions. The bandage is manufactured from a single liquid-permeable foamed polyurethane sheet possessing a liquid-permeable porous pressure sensitive adhesive layer on its skin-contacting side. Selected areas of the sheet are heat compressed to provide first and second wound site-securing tab portions on each side of a foamed pad portion which has not been subjected to compression. Both the tabs and the pad provide ready absorption and transfer of fluids from the wound site. When the pad approaches its maximum wound exudate-carrying capacity, the tabs wick excess exudate.

Were wound exudate-carrying capacity the sole or principal consideration in the construction of an effective wound dressing, the foam bandage of U.S. Pat. No. 4,655,210 could be said to possess an advantage over the aforementioned common strip bandage whose adhesive tab portions are incapable of wicking wound exudate. However, at least as important, if not more important, than a high wound exudate-carrying capacity is the ability of a wound dressing to adhere to the site of application throughout the entire period of its expected functional life. A premature loss of adherency will require more frequent application of fresh bandages and consequently, a greater cost to the consumer. The very ability of the tab portions of the bandage of U.S. Pat. No. 4,655,210 to wick excess wound exudate is itself a disadvantage where long term adherency is concerned. Thus, once wound exudate makes contact with the adhesive layer, it begins to infiltrate the adhesive compromising the adherency of the bandage to the skin.

SUMMARY OF THE INVENTION

It is an object of the present invention to provide a wound dressing possessing a wound exudate-absorbing component of cellular structure and at least one wound dressing-securing component having little if any capacity for absorbing aqueous substances such as wound exudate.

It is another particular object of the invention to provide such a wound dressing in which the wound exudate-absorbing component contains a solid or semi-solid material which liquefies at or about skin temperature and, when liquid, maintains the wound site in a moist condition and/or functions as a release agent to prevent the wound exudate-absorbing component from adhering to the wound site during the course of healing.

It is yet another particular object of the invention to incorporate a quantity of medicament, e.g., an antibiotic, antiseptic, local anaesthetic, antipruritic, counterirritant, etc., which promotes, assists or is otherwise beneficial to the wound healing process in the aforementioned solid or semi-solid liquefiable material, the latter additionally functioning as a carrier for the medicament and, when liquid, making the medicament available to the wound site.

In keeping with these and other objects of the invention, there is provided a wound dressing comprising:

a) a wound exudate-absorbing component of flexible cellular structure fabricated from a flexible cellular thermoplastic resin workpiece;

b) at least one wound dressing-securing component adjacent the wound exudate-absorbing component and fabricated from the same workpiece as the latter, the wound dressing-securing component possessing a layer of adhesive on its skin-contacting surface; and, c) means for substantially preventing the passage of wound exudate or other fluent substance from the wound exudate-absorbing component into the wound dressing-securing component.

In contrast to the foam bandage of U.S. Pat. No. 4,655,210 whose adhesive tab portions have the capacity for absorbing significant quantities of wound exudate, a capability of questionable value given the possibility of a diminution in adherency of the bandage to the skin once wound exudate makes contact with the adhesive layer on the skin-contacting surface of the bandage, the wound dressing-securing component of this invention has little, if any, capacity for absorbing aqueous substances such as wound exudate thereby minimizing, if not eliminating, the risk that wound exudate will make contact with its adhesive layer and compromise the adherency of the dressing to the skin.

BRIEF DESCRIPTION OF THE DRAWINGS

FIG. 1 illustrates in side elevational view an embodiment of a wound dressing in accordance with this invention applied to a wound site;

FIG. 2 is an illustration in side elevational view of another embodiment of the wound dressing of this invention featuring a cushioning component superimposed upon the wound exudate-absorbing component; and FIGS. 3 and 4 illustrate perspective view embodiments of the wound dressing of this invention in which the dressing-securing component is provided as a continuous region surrounding the wound exudate-absorbing component.

DESCRIPTION OF THE PREFERRED EMBODIMENTS

One embodiment of a wound dressing in accordance with this invention is shown generally in FIG. 1 at 10. The wound dressing features an optional flexible, liquid-impermeable film or coating 11 upon its entire upper exterior surface to prevent diffusion of wound exudate to the upper exposed side of the wound dressing. However, if desired, optional film or coating 11 can be confined to the upper exterior surface of cellular wound exudate-absorbing component 15 since this is the only region of the dressing that would benefit from a liquid-impermeable film or coating when the addition of a liquid barrier property is desired.

Wound dressing 10 is positioned upon wound site 19 directly over wound bed 18 containing serous exudate, a largely aqueous substance. Wound dressing 10 is secured to wound site 19 by first and second straps 12 and 13 coated on their skin-contacting sides with pressure-sensitive adhesive 14. Straps 12 and 13 are formed from the same flexible, cellular thermoplastic resin workpiece as wound exudate-absorbing component 15 and together with the latter, form a seamless unitary whole. Straps 12 and 13 can be formed by compressing and heating certain sections of the aforementioned workpiece as a result of which such sections acquire a collapsed cell structure which is essentially non-absorbing for aqueous substances, such as wound exudate (in contrast to wound exudate-absorbing component 15 which exhibits relatively high aqueous liquid-sorbing capability). The collapsed cell structure can exist uniformly throughout the entirety of straps 12 or 13 or it can be confined to strips or zones adjacent the transverse edges of wound exudate-absorbing component 15. In addition to, or in lieu of, this collapsed cell structure, a bead or line of barrier material, preferably of sufficient flexibility to flex with the wound dressing when applied to the skin, can be formed at or near the juncture of wound exudate-absorbing component 15 and each of straps 12 and 13 to prevent the wicking of any substance, whether it be wound exudate or any other flowable material, into the straps where it could make contact with, and consequently lessen the effectiveness of, the adhesive. Suitable barrier materials include molten resins such as polyethylene or polypropylene, which solidify on cooling, finely powdered resins which can be heat-coalesced into a solid barrier, e.g., polyethylene or polypropylene powders, hardenable or curable resins which form on polymerization or crosslinking, e.g., acrylic resins, and solvent-containing resins which solidify on evaporation of the solvent, e.g., cellulosic putty.

If desired, the wound site-contacting surface of wound exudate-absorbing component 15 can be treated or modified, e.g., by addition of an abherent perforate film or coating, to prevent or minimize adherence of such surface to the wound site. In a preferred embodiment, wound exudate-absorbing component 15 is provided with a quantity of a solid or semi-solid material which liquefies at or about ambient skin temperature, or from about 25° to about 45° C., and when liquid maintains the wound site in a moist condition and/or functions as a release agent to prevent the wound exudate-absorbing component from adhering to the wound site during the course of healing. Suitable materials having one or both of these capabilities are known in the art although for wholly unrelated applications. For example, U.S. Pat. No. 5,160,738, describes a mixture of low and high melting value polyol fatty acid polyesters which through appropriate blending can be made to liquefy, i.e., melt, at or about skin temperature. Similarly, U.S. Pat. No. 5,204,104 describes a mixture of polyethylene glycols which can be formulated to melt at or about skin temperature: a first polyethylene glycol having a relatively high viscosity and a melting temperature in excess of the temperature of the human body, a second polyethylene glycol having a melting temperature less than the temperature of the human body and a third polyethylene glycol exhibiting lubricity or emolliency. U.S. Pat. No. 5,334,737 describes a solid silicone ester which liquefies at ambient skin temperature. Still another example of a useful liquefiable material which can be incorporated in wound exudate-absorbing component 15 to provide either or both of the aforestated functions are microspheres made from one or a mixture of fatty substances liquefying at or about skin temperature and an active medicament employing known or conventional techniques, e.g., the spraying procedure described in U.S. Pat. No. 5,292,512. The contents of aforementioned U.S. Pat. Nos. 5,160,738, 5,204,104, 5,334,737 and 5,292,512 are incorporated by reference herein. Additional useful liquefiable materials include cocoa butter and cocoa butter substitutes, hydrogenated vegetable oils, hard fats, glycerinated gelatin, nonionic surface active agents such as polyethylene sorbitan fatty acid esters and polyoxyethylene stearates alone or in combination with other materials to provide a wide range of melt temperatures and consistencies, etc. Those skilled in the art are familiar with many other types of liquefiable materials that can be utilized as the wound moisturizing/wound site releasing material in the wound dressing of this invention. When incorporating the liquefiable material in exudate-absorbing component 15, it may be advantageous to concentrate the material in the central region of this component and away from straps 12 and 13 in order to minimize the possibility that any of the material could be wicked into the straps.

The incorporation of a solid or semi-solid liquefiable material in exudate-absorbing component 15 offers the additional advantage that it can be used as a carrier for one or more medicaments, e.g., an antibiotic, antiseptic, local anesthetic, antipruritic, counterirritant, etc., which promotes, assists or is otherwise beneficial to the wound healing process. Upon liquefying, the material migrates toward the wound site making the medicament(s) incorporated therein available to the wound. Thus, skin temperature activates the release of the medicament(s) present in the wound dressing of this invention and places the medicament(s) in direct contact with the wound site for the most beneficial therapeutic action possible. Suitable medicaments for incorporation into the liquefiable material include one or more of the following at the usual levels: local anesthetics such as benzocaine, butamben, dibucaine, bibucaine hydrochloride, dimethisoquin hydrochloride, dyclonine hydrochloride, lidocaine, lidocaine hydrochloride, pramoxine, tetracaine and tetracaine hydrochloride; antiseptics such as benzalkonium chloride, chlorhexidine gluconate, glutaral, hexachlorophene, iodine, povidone-iodine, mafenide acetate, nitrofurazone, silver sulfadiazone; and, antibiotics such as bacitracin, bacitracin zinc, chlortetracycline hydrochloride, neomycin sulfate, polymyxin B sulfate and oxytetracycline hydrochloride.

The flexible, cellular (i.e., foamed) thermoplastic resin workpiece from which wound dressing 10 is manufactured can vary considerably in its properties: e.g., it can have a thickness of from about 1/16 to about 2 in., a void volume of up to about 98 percent, an average cell size of from about 200 to about 2,000 microns and a density of from about 1.3 to about 10 lb/ft$^3$. Among the cellular thermoplastic resins that can be used are polyurethanes, latex foam rubbers, poly(vinyl chloride) resins, silicone resins, and the like. For details regarding a particular cellular resin, see, e.g., standard reference works such as the "Encyclopedia of Polymer Science and Technology", Mark et al. eds., 2nd ed., Vol. 3, pp. 6–14 (Wiley, 1985). The cell structure of the workpiece can be reticulated or non-reticulated and is advantageously of the open cell type to achieve good rates of wound exudate absorption. Filtercrest® and Feltcrest® reticulated polyurethane foams available from Crest Foam Industries, Inc., 100 Carol Place, Moonachie, N.J. 07074 are suitable for use as workpiece 80. Other suitable polyurethane foams include those disclosed in U.S. Pat. Nos. 3,975,567, 3,978,855, 4,655,210, 4,960,594, 5,154,928 and 5,164,421, the contents of which are incorporated by reference herein.

Wound dressing 10 can possess a liquid-impermeable film or layer 11 as an optional component where barrier properties are desired. Optional liquid-impermeable component 11 can be provided as a thermoplastic film, e.g., a polyethylene film of from about 0.005 to about 0.01 cm thickness bonded to the upper surface of the workpiece, or as a layer of material which imparts liquid barrier properties to the upper surface of the workpiece, e.g., a coating of molten polyethylene resin which on application to said surface infiltrates the uppermost zone of cells and on solidification provides a liquid-impermeable stratum to a depth of from about 0.01 to about 0.1 cm. As a matter of manufacturing convenience, liquid-impermeable component 11 can be applied to the entire upper surface of the workpiece; however, where barrier properties are desired, liquid-impermeable component 11 can be confined to just those areas of the upper surface of the workpiece which are destined to become cellular wound exudate-absorbing component 15. As an alternative to the aforedescribed procedure of applying optional liquid-impermeable component 11 to the workpiece, this component can be applied to the upper surface of cellular wound exudate-absorbing component 15 following reshaping of the workpiece as described below. So-called integral skin foams can also be used as the workpiece; such foams possess a relatively dense liquid-impermeable skin surface and a liquid-absorbing cellular core. Splitting an integral skin foam into two layers provides two workpieces each of which possesses a liquid-impermeable surface and a liquid-absorbing surface. Such workpieces dispense with the need to add a separate liquid-impermeable component when barrier properties are desired.

As previously described, the wound dressing of this invention can be formed by selectively applying heat and pressure to part or all of those regions of the workpiece which are to become the wound dressing-securing component(s) thereof. The application of heat and pressure causes the collapse of the cellular structure in these regions making them substantially non-absorbent for, or impermeable to, liquids such as wound exudate, liquefied wound moisturizing/wound site releasing material, etc. Those regions of the workpiece which have not received the heat and compression treatment will retain the cellular structure of the original workpiece and thus function as the wound exudate-absorbing component(s) of the wound dressing of this invention. U.S. Pat. No. 4,655,210 referred to supra describes a workpiece reshaping method which can be adapted to the construction of the wound dressing herein. However, when relying solely on a collapsed cell structure to prevent wicking of liquid into the wound dressing-securing component(s), e.g., straps 12 and 13 of wound dressing 10, the degree of cell collapse (or cell compression) must be greater than that sought in U.S. Pat. No. 4,654,210. How much greater will depend upon the characteristics of the workpiece and can be readily determined in a specific case by simple experimental testing.

The alternative approach to rendering the wound dressing-securing component(s) of the wound dressing herein essentially non-wicking, i.e., incorporating a liquid-impermeable barrier between the regions of the workpiece intended to become the wound dressing-securing components and the regions intended to become the wound exudate-absorbing components, can be achieved employing known and conventional techniques. For example, a line of molten polyethylene can be forced under moderate pressure into the cellular structure of the workpiece in accordance with a defined pattern. Upon cooling and solidifying, the polyethylene functions as a barrier to prevent passage of liquid from one side to the other. Similarly, resin powders that can be melted into a solid line of polymer, curable resins and solvent solutions of resins, can also be introduced into the cellular structure of the workpiece in the desired pattern to mark off the boundaries between the wound dressing-securing component(s) and the wound exudate-absorbing component(s). It is, of course, within the scope of this invention to utilize both approaches, i.e., collapsing the cellular structure in selected regions of the workpiece and providing a liquid impermeable barrier, to render the wound dressing-securing component(s) non-sorbent for fluent substances.

FIGS. 2–4 illustrate other embodiments of the wound dressing of this invention. Dressing 20 of FIG. 2 shows optional flexible liquid-impermeable film or layer 21 disposed within the interior structure of the dressing in contrast to its surface as in the case of dressing 10 of FIG. 1. On the side of film or layer 21 facing wound site 29 with its exudate-containing wound bed 26 is a region of wound exudate-absorbing component 25 containing an antiseptic, antibiotic drug and/or other medicament 28, preferably in a liquefiable carrier as described above, which is capable of diffusing or migrating from this region into the wound bed. On the other side of film or layer 21 is a region of cellular structure 27 which functions as a cushioning component providing the wound site with additional protection against trauma. Straps 22 and 23 with their coating of adhesive 24 provide the dressing-securing component as in the embodiment of FIG. 1. The procedures for manufacturing wound dressing 20 are similar to those employed for manufacturing wound dressing 10. A single workpiece sheet can be folded over upon itself with layer 21 positioned in between the assembly or a separate workpiece sheet can be superimposed upon another to effect the same arrangement. Thereafter, heat and compression simultaneously applied to selected regions of the workpiece assembly will cause the cellular structure of such regions to collapse and, at the same time, heat seal the workpiece layers to each other to provide wound dressing 20.

In wound dressing 30 of FIG. 3, wound dressing-securing component 32 is provided as a continuous band of pressure-sensitive adhesive-coated material of collapsed cell structure surrounding wound exudate-absorbing component 31 (shown in the inverted position). Peelable film 33 covers the wound-contacting surface of the dressing until the latter is ready to be used. Wound dressing 40 of FIG. 4 is similar to that of FIG. 3 except for having a circular configuration. Otherwise, components 41, 42 and 43 correspond to components 31, 32 and 33 of the embodiment shown in FIG. 3.

Although several embodiments of the wound dressing and method for manufacturing a wound dressing in accordance with the present invention have been described in detail, it is understood that obvious variations can be made without departing from the spirit and scope of the invention as defined by the appended claims.

What is claimed is:

1. A wound dressing for application to a wound site comprising:

a) a wound exudate-absorbing component constructed from a flexible cellular structure fabricated from a flexible cellular thermoplastic resin workpiece, the wound exudate-absorbing component having a wound contacting surface;

b) at least one wound dressing-securing component having a skin-contacting portion, the wound dressing-securing component integral with and adjacent the wound dressing-absorbing component and being fabricated from the same workpiece as the wound exudate-absorbing component, the wound dressing-securing component possessing a layer of adhesive on its skin-contacting surface; and c) a region of collapsed cellular structure where the wound exudate-absorbing component and the wound dressing-securing component meet, the region of collapsed cellular structure formed by compressing and heating the flexible cellular thermoplastic resin workpiece and being essentially non-absorbing for aqueous substances for substantially preventing the passage of wound exudate from the wound-absorbing component, the wound dressing being fabricated from a single workpiece.

2. The wound dressing of claim 1 wherein the wound exudate-absorbing component possesses a liquid-impermeable barrier film to prevent diffusion of wound exudate to the upper exposed side of the wound exudate-absorbing component.

3. The wound dressing of claim 1 wherein the region of collapsed cellular structure is coextensive with the wound dressing-securing component.

4. The wound dressing of claim 3 wherein the wound dressing-securing component includes first and second strap members of collapsed cell structure extending from opposite sides of the wound exudate-absorbing component.

5. The wound dressing of claim 3 wherein the wound dressing-securing component includes a continuous band of collapsed cell structure surrounding the wound exudate-absorbing component.

6. The wound dressing of claim 1 wherein the wound-contacting surface of the wound exudate-absorbing component is treated to reduce adherence of such surface to the wound site.

7. The wound dressing of claim 2 wherein the liquid-impermeable barrier film is disposed within the interior of the wound exudate-absorbing component.

8. The wound dressing of claim 1 wherein the wound exudate-absorbing component contains a material which liquefies at or about skin temperature and, when liquid, maintains the wound site in a moist condition and functions as a release agent to prevent the wound exudate-absorbing component from adhering to the wound site.

9. The wound dressing of claim 8 wherein the liquefiable material contains at least one medicament.

10. The wound dressing of claim 9 wherein the medicament is at least one member of the group consisting selected from antibiotic, antiseptic, local anesthetic, antipruritic and counterirritant.

* * * * *